United States Patent [19]
Akashi et al.

[11] Patent Number: 4,568,753
[45] Date of Patent: Feb. 4, 1986

[54] RUST-PREVENTIVE AGENT

[75] Inventors: Sumio Akashi; Katsushige Koge, both of Yamaguchi, Japan

[73] Assignee: Sanshin Kagaku Kogyo Co., Ltd., Yanai, Japan

[21] Appl. No.: 553,434

[22] Filed: Nov. 18, 1983

[51] Int. Cl.[4] ............................................. C07D 277/62
[52] U.S. Cl. ..................................... 548/174; 252/390; 252/391; 252/402; 548/161
[58] Field of Search ..................... 252/390, 391, 402; 548/161, 174

[56] References Cited

U.S. PATENT DOCUMENTS

| 2,544,001 | 3/1951 | Zerbe | 252/150 |
| 2,638,449 | 5/1953 | White et al. | 252/51.5 |
| 2,638,450 | 5/1953 | White et al. | 252/51.5 |
| 3,537,999 | 11/1970 | Kennedy | 252/391 |
| 3,966,623 | 6/1976 | Krug et al. | 252/391 |
| 4,235,838 | 11/1980 | Redmore et al. | 252/391 |
| 4,432,847 | 2/1984 | Fields | 252/391 |

Primary Examiner—Paul Lieberman
Assistant Examiner—Willie J. Thompson
Attorney, Agent, or Firm—David A. Jackson; Daniel H. Bobis

[57] ABSTRACT

Improved rust-preventive compounds are provided which are strongly effective with both iron and copper metals. The compound of the invention comprise benzothiazole-substituted carboxylic acids, and their salts. Suitable salts may include alkali metal, alkaline earth metal, ammonium and substituted ammonium salts.

18 Claims, No Drawings

RUST-PREVENTIVE AGENT

BACKGROUND OF THE INVENTION

1. Field of the Invention

The present invention relates generally to rust-preventive agents and particularly to rust-preventive agents that are effective with iron and/or copper metals.

2. Description of the Prior Art

Conventionally used rust-preventive agents for iron and iron base alloys include materials such as sodium nitrite, organic and inorganic phosphoric acid compounds and their salts, and chromium-containing compounds, including simple and complex chromates. These agents, however, suffer various drawbacks. For example, sodium nitrite is a suspected carcinogen because it reacts with a means to produce nitroso compounds which are believed to be involved in the development of cancer in animals. Also, as chromium containing compounds exhibit toxicity due to the presence of chromium ions, and since phosphorous compounds offer an undesirable nutritive medium, the employment of these compounds as rust preventive agents has been accordingly limited.

Despite the above, sodium nitrite is widely used as a rust-preventive agent for iron and its alloys, as there is no such strongly effective water soluble agent available. While sodium nitrite is effective with iron and its alloys, it does not possess the comparable rust or corrosion inhibitive capability with respect to copper and copper base alloys. The result of the deficiency is that, in the instance where iron-copper alloys are to be treated for rust prevention, sodium nitrite offers limited protection to the metal.

A further drawback in the use of sodium nitrite is its limited useful life when disposed as a coating on the metal base. Sodium nitrite may be dissolved by the attack of certain microorganisms, and resultingly a coating containing this rust-preventive agent looses its effectiveness.

Other rust-preventive agents, include aliphatic acids, including aliphatic carboxylic acids. These materials, however are inferior as rust-preventive agents and are not widely used. Other known rust-preventive agents for copper-containing materials include benzotriazole, and its derivative, 2-mercaptobenzothiazolate and related compounds. These materials, however, have not exhibited rust-preventive capability with iron and iron-containing alloys.

A need therefore exists for a rust-preventive compound which offers a broad spectrum of capability with respect to both iron and copper-containing metals and at the same time exhibits extended effective life in solution.

SUMMARY OF THE INVENTION

In view of the defects of the conventional agents, the inventors of the present invention have developed a new rust-preventive agent which is effective to both iron and coppers and to their respective alloys, including iron-copper alloys, and which has stable and long standing effect. The compounds of the invention comprise benzothiazole-substituted carboxylic acids, and their salts, including alkali metal, alkaline earth metal, ammonium, or substituted ammonium salts. The compounds of the invention exhibit rust-preventive capability much greater than that of conventional carboxylic acids, and are stably effective with copper metals as well.

In a particular embodiment, the present invention comprises a rust-preventive compound of the general formula:

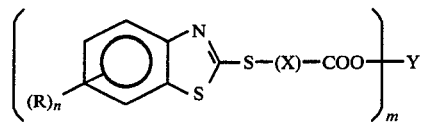

wherein R is selected from amino, methyl, chloro, carboxy and hydroxyl groups; n is an integer of 0 through 2; X is selected from straight- or branched-chain, divalent aliphatic hydrocarbon radicals having 0 through 5 carbon atoms, and divalent aromatic hydrocarbon radicals having 6 through 10 carbon atoms; Y is selected from hydrogen, alkali metals, alkali earth metals, ammonium, and substituted ammonium groups; and m is an integer having a value equal to the valence number.

Suitable salts of the foregoing compounds may be prepared with alkali metals such as lithium, sodium, and potassium and alkaline earth metals such as magnesium, calcium and the like. In particular, sodium or potassium salts are most effective when the compounds is to desirably possess improved water-solubility.

In addition, and as mentioned earlier, ammonium and substituted ammonium salts such as amines may be utilized, as these are found to improve the rust-preventive capabilities of the resulting compound. For example, the ammonium group offers improved water solubility in conjunction with improved rust-preventive capability and is particularly preferred in certain instances.

The rust-preventive agents or compounds of the present invention may be utilized in a variety of environments and in particular are well suited for use in cooling water systems for chemical plants which are inevitably turbulent and are prone to rust and corrosion from the circulating waters. Also, the agents of the present invention may be utilized as a component in anti-freeze liquids for motor vehicles and the like, for other heating systems, and as a heat exchange medium in solar energy storage and transfer systems, as an anti-rust ingredient in certain lubricating oils and paints, and as a rust-preventive agent for various concretes and other operative liquids having a high water content. A particular utility of the present invention is its use in anti-freeze liquids for vehicles and in heating media for solar systems that use copper-iron alloy hardware.

As mentioned earlier, the rust-preventive agents of the present invention and in particular the compounds specified above offer improved rust-inhibitive capability for a broader spectrum of metal substrates, and can now be utilized on copper as well as iron base alloys and alloys containing both metals with efficacious results. Similarly, the present compounds are not adversely affected by turbulent fluid conditions or bacterial attack and offer substantial improvement in useful life in operation.

Accordingly, it is a principal object of the present invention to provide a rust-preventive agent which is useful on both copper and iron-base alloys.

It is a further object of the present invention to provide a rust preventive agent as aforesaid which has improved useful life and resists bacterial attack and degradation.

It is a yet further object of the present invention to provide a rust-preventive agent as aforesaid that may be used in turbulent liquids of high water content and will effectively prevent the development of rust or corrosion within the containing hardware.

Other objects and advantages will become apparent to those skilled in the art from a review of the ensuing description.

DETAILED DESCRIPTION OF THE INVENTION

The present invention concerns certain rust-preventive agents offering a broad spectrum of rust-preventive capability for both iron and copper-base alloys. The agents of the present invention are compounds comprising benzothiazole-substitute carboxylic acids, their salts and homologs thereof. In particular, the salts of such carboxylic acids may include alkali metal, alkaline earth metal, ammonium and substituted ammonium salts, with substituted ammonium or amine salts preferred by virtue of the improvement in both water-solubility and rust-preventive capability that is imparted to the resulting compounds.

In particular, the compounds of the present invention may be prepared in accordance with the general formula:

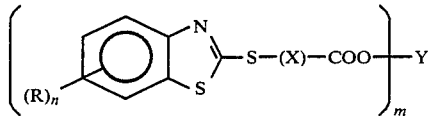

wherein R is selected from amino, methyl, chloro, carboxy and hydroxyl groups; n is an integer of 0 through 2; X is selected from straight- or branched-chain, divalent aliphatic hydrogen radicals having 0 through 5 carbon atoms, and divalent aromatic hydrocarbon radicals having 6 through 10 carbon atoms; Y is selected from hydrogen, alkali metals, alkali earth metals, ammonium, and substituted ammonium groups; and m is an integer having a value equal to the valence number.

As mentioned earlier, the compounds of the present invention may be prepared by the reaction of the sodium salt of either 2-mercaptobenzothiazole or a substituted 2-mercaptobenzothiazole, and a halogenated alkyl carboxylic acid or allyl carboxylic acids. Examples of suitable compounds prepared in accordance with the present invention include 2-benzothiazyl thioacetic acid, 6-amino-2-benzothiazyl thioacetic acid, 5-carboxy-2-benzothiazyl thioacetic acid, 6-hydroxy-2-benzothiazyl thioacetic acid, 2-benzothiazyl thioformic acid, 3-(4-methyl-2-benzothiazylthio)-propionic acid, 3-(6-hydroxy-2-benzothiazylthio)-propionic acid, 3-(4,6-dimethyl-2-benzothiazylthio)-propionic acid, 2-(2-benzothiazylthio)-propionic acid, 3-(5-chloro-2-benzothiazylthio)-propionic acid, 2-(4-methyl-2-benzothiazylthio)-propionic acid, 5-(2-benzothiazylthio)-valeric acid, 3-(2-benzothiazyl thio)-valeric acid, 5-(5,6-dihydroxy-2-benzothiazyl thio)-valeric acid, 5-(4-methyl-2-benzothiazylthio)-valeric acid, 3-(2-benzothiazylthio)-acrylic acid, 3-(4-methyl-2-benzothiazylthio)-arcylic acid, 4-(2-benzothiazylthio)-butyric acid, 4-(4-methyl-2-benzothiazylthio)-butyric acid, 4-(6-amino-2-benzothiazylthio)-butyric acid, 2-(2-benzothiazylthio)-benzoic acid, and 2-(4-methyl-2-benzothiazylthio)-benzoic acid. The foregoing list is exemplary only, and should not be considered limitative, as other substituted acids may be prepared and used within the scope of the invention.

As mentioned earlier, the benzothiazole-substituted carboxylic acids of the invention may be prepared by reacting the sodium salt of substituted or unsubstituted 2-mercaptobenzothiazole and a halogenated saturated or unsaturated carboxylic acid such as an alkyl carboxylic acid or allyl carboxylic acid. Preferably, the mercaptobenzothiazole salt is disposed in a solvent such as methanol and is thereafter heated slightly above room temperature and preferably to about 40° C. A similarly constituted solution of the sodium salt of the halogenated carboxylic acid is then added to the heated solution and the resulting solution is thereafter heated under slight agitation, such as by circulation. The solvent may thereafter be distilled off, leaving the substituted acid in crystal form.

In the instance where the salts of the substituted acids of the present invention are to be prepared, the crystalline product may be reacted with an equivalent quantity of the hydroxide of the intended salt forming substituent, e.g. sodium hydroxide, ammonimum hydroxide, etc. Naturally the salt-forming substituent may be provided in alternate reactive forms within the scope of the invention.

As mentioned earlier, the various salts of the substituted acids of the present invention exhibit a combination of improved properties. Thus, for example, suitable salts of the foregoing substituted acids may be prepared with alkali or alkaline earth metals, ammonium and substituted ammonium or amine substitutents. Alkali metal salts may be prepared with lithium, sodium and potassium, while alkaline earth metal salts may be prepared with magnesium, calcium, strontium and the like. In the instance where rust-preventive capability is desired in combination with improved water solubility, the alkali metal salts of sodium or potassium are preferred.

The ammonium and substituted ammonium or amine salts of the substituted acids of the invention are also preferred as they improve both the rust-preventive capability while at the same time offering improvement in water solubility. In particular, the quaternary ammonium group is preferred for imparting this combination of improved properties. Suitable quaternary ammonium groups are those bearing the general formula —H.Z, wherein Z is a substituent selected from the group consisting of ammonia, aliphatic amines, alicyclic amines, heterocyclic amines, and polyethylene polyamines.

Suitable aliphatic amines include monoethanolamine, diethanolamine and triethanolamine; alicyclic amines include cyclohexylamine and dicyclohexylamine; heterocyclic amines include morpholine and pyridine; and, polyethylene polyamines include diethylene triamine, triethylene tetramine and tetraethylene pentamine.

As mentioned earlier, the rust-preventive compounds of the present invention may be used in a variety of environments, and are particularly well suited for aqueous cooling systems wherein corrosion due to the presence of water inevitably results. Thus, such cooling water systems as are used in chemical plants and the like may incorporate a quantity of the rust-preventive agent of the present invention. Likewise, hot water heating systems, anti-freeze solutions for motor vehicles and the like, heat-transfer media for solar energy storage and transfer systems, rust-preventive oils and paints, and similar agents for incorporation into concrete compositions, and other operative liquids having a high water content are contemplated for inclusion therein of the present rust-preventive agents. The present agent is particularly effective when utilized in anti-freeze fluids for motor vehicles and as the heat-transfer medium in heating systems utilizing components prepared from iron-copper alloys.

Naturally, the agent of the present invention may be incorporated in a variety of compositions as mentioned above, and can further be utilized in combination with conventional rust-preventive agents utilized in various materials. Thus, the present invention may also include a rust-preventive composition comprising the agent of the present invention and a suitable carrier, such as a paint, oil or the like.

The present invention will be better understood from a review of the following illustrative examples.

EXAMPLE I

The substitute carboxyclic acid salts of the invention were prepared in the following manner. 20 parts of 2-mercaptobenzothiazole sodium salt was added to 200 parts of methanol, and the solution was heated to 40° C. under agitation. Then a solution of 14 parts sodium salt of β-chloropropionic acid in methanol, was dropped onto the heated solution for 30 minutes, and the obtained solution was subsequently heated under circulation. The methanol was thereafter distilled off. A crystalline product was recovered, which was then washed with ample amount of cooled water and cooled. 23 parts of white crystalline product (yield: 93%) was obtained which was identified as 3-(2-benzothiazylthio) propionic acid. Its melting point was 141°–143° C. (theoretical point: 142°–143° C.). The product was reacted with an equivalent amount of sodium hydroxide so as to produce the sodium salt of 3-(2-benzothiazylthio)-propionic acid which, in turn, was used in examples mentioned later.

EXAMPLES II–XIV

Additional compounds were prepared in accordance with the procedure outlined in Example I above. These compounds are listed in the table following later on herein and as will be described with reference to Example XV below, all exhibited improved rust-preventive capability.

EXAMPLE XV

The compounds prepared in accordance with Examples I–XIV, above, were tested to determine their rust-preventive capability. In addition to the 14 examples of the invention, 7 control solutions or examples were likewise prepared, these controls comprising a blank containing water as defined herein, and the remaining 6 containing, respectively, sodium nitrite, 2-mercaptobenzothiazole sodium salt, benzotriazole, triethanol amine, sodium sebacate and triethanol amine salt of sebacic acid.

The foregoing compounds, including both the 6 control compounds and the 14 compounds prepared in accordance with the present invention were added to a quantity of water having the following water analysis.

| Water Quality Analysis | |
| --- | --- |
| pH (at 23° C.) | 7.2 |
| Electric conductivity (μs/cm) | 13.3 |
| M-alkali value (CaCO3)(ppm) | 28 |
| Total hardness (CaCO3)(ppm) | 36 |
| Chlorine ion (Cl−)(ppm) | 15 |
| Total iron (Fe)(ppm) | 0.34 |

The following testing procedure was adopted and used. 350 ml of chemicals (product of the invention) was introduced into a 500 ml colben. A test piece (steel plate SPCC, 50φ×1 mm; copper plate TCuPl, 50φ×1 mm) was polished with water-resistant polishing paper No. 320, and was rinsed with 10% NaOH to remove any remaining surface oils. Test pieces were then washed with water, thereafter washed with acetone, then dried and fitted to agitating bars connected to an agitating motor. The test piece was then positioned into the center part of the liquid in the colben retained at 50° C. The test piece was rotated at 120 r.p.m. for one week. Liquid level was maintained at a predetermined level by adding additional test water as the liquid level dropped.

After one week passed, the test pieces were removed from the solution and were observed. The degree of corrosion was calculated on the basis of corrosion loss of the test piece. The following table shows the test results, in which corrosion degree is expressed as a relationship of corrosion loss (mg)/days tested/surface area (dm$^2$) of test piece.

TABLE

| No. | Constituent | Added density (ppm) | Corrosion Degree Steel | Corrosion Degree Copper | Copper Surface Color Change |
| --- | --- | --- | --- | --- | --- |
| Control 1 | blank | | 25.3 | 3.31 | color change |
| Control 2 | sodium nitrite | 200 | 3.2 | 6.91 | color change |
| Control 3 | triethanol amine | 200 | 5.9 | 8.21 | color change |
| Control 4 | benzotriazole | 200 | 12.5 | 0.51 | no change |
| Control 5 | sodium salt of 2-mercapto-benzothiazole | 200 | 11.3 | 0.59 | no change |
| Control 6 | sodium sebacate | 200 | 5.2 | 1.83 | small change |
| Control 7 | triethanol amine salt of sebacic acid | 200 | 3.9 | 4.00 | change |
| Example 1 | potassium salt of 2-benzothiazyl thioacetic acid | 200 | 3.7 | 0.61 | no change |
| Example 2 | triethanol amine salt of 6-amino-2-benzo thiazylthio acetic acid | 200 | 4.1 | 0.92 | small change |
| Example 3 | sodium salt of 3-(2-benzo thiazylthio)-acid | 200 | 3.0 | 0.59 | no change |
| Example 4 | triethanol amine salt of 3-(4-methyl-2-benzothiazyl thio)-propionic acid | 200 | 3.1 | 0.71 | no change |
| Example 5 | dicyclohexyl amine salt of 5-(3-benzothia zylthio)-valeric acid | 200 | 5.3 | 1.41 | small change |
| Exmple 6 | Calcium salt | 200 | 5.1 | 0.93 | small |

TABLE-continued

| No. | Constitutent | Added density (ppm) | Corrosion Degree Steel | Corrosion Degree Copper | Copper Surface Color Change |
|---|---|---|---|---|---|
| | of 5-(4,6-dimethyl-2-benzothiazyl thio)-valeric acid | | | | change |
| Example 7 | (sodium salt of 2-(2-benzo thiazylthio)-benzoic acid | 200 | 3.2 | 0.61 | no change |
| Example 8 | ammonium salt of 2-(2-benzo thiazylthio)-acrylic acid | 200 | 7.2 | 1.92 | small change |
| Example 9 | diethanol amine salt of 2-(2-benzothiazyl thio)-propionic acid | 200 | 3.0 | 0.70 | no change |
| Example 10 | morpholine salt of 2-(4-methyl-2-benzothiazyl thio)-propionic acid | 200 | 3.1 | 0.79 | no change |
| Example 11 | sodium salt of 4-(2-benzothia zylthio)-butyric acid | 200 | 3.7 | 0.59 | no change |
| Example 12 | triethylene tetramine salt of 3-(6-hydroxy-2-benzo thiazylthio)-propionic acid | 200 | 3.8 | 1.02 | small change |
| Example 13 | (triethanol amine salt of 3-(5-chloro-2-benzothia zylthio)-propionic acid | 200 | 6.9 | 1.50 | small change |
| Example 14 | sodium salt of 5-carboxy-2-benzo thiazylthio-acetic acid | 200 | 3.2 | 0.65 | no change |

From the examples above, it is clear that carboxylic acid salts of benzothiazole rings are particularly effective as rust-preventive agent for iron and copper metals.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A rust preventive compound comprising a compound of the general formula:

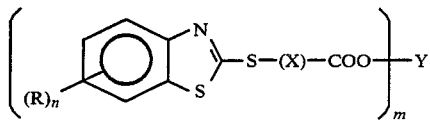

wherein R is selected from amino, methyl, chloro, carboxy and hydroxyl groups; n is an integer of 0 through 2; X is selected from straight- or branched-chain, divalent aliphatic hydrocarbon radicals having 0 through 5 carbon atoms, and divalent aromatic hydrocarbon radicals having 6 through 10 carbon atoms; Y is selected from hydrogen, alkali metals, alkali earth metals, ammonium, and substituted ammonium groups; and m is an integer having a value equal to the valence number.

2. The rust preventive compound of claim 1 wherein Y is hydrogen, and said compound is selected from the group consisting of 2-benzothiazyl thioacetic acid, 6-amino-2-benzothiazyl thioacetic acid, 6-hydroxy-2-benzothiazyl thioacetic acid, 5-carboxy-2-benzothiazyl thioacetic acid, 2-benzothiazyl thioformic acid, 3-(4-methyl-2-benzothiazylthio)-propionic acid, 3-(6-hydroxy-2-benzothiazylthio)-propionic acid, 3-(4,6-dimethyl-2-benzothiazylthio)-propionic acid, 2-(2-benzothiazylthio)-propionic acid, 3-(5-chloro-2-benzothiazylthio)-propionic acid, 2-(4-methyl-2-benzothiazylthio)-propionic acid, 5-(2-benzothiazylthio)-valeric acid, 3-(2-benzothiazyl thio)-valeric acid, 5-(5,6-dihydroxy-2-benzothiazyl thio)-valeric acid, 5-(4-methyl-2-benzothiazylthio)-valeric acid, 3-(2-benzothiazylthio)-acrylic acid, 3-(4-methyl-2-benzothiazylthio)-arcylic acid, 4-(2-benzothiazylthio)-butyric acid, 4-(4-methyl-2-benzothiazylthio)-butyric acid, 4-(6-amino-2-benzothiazylthio)-butyric acid, 2-(2-benzothiazylthio)-benzoic acid, and 2-(4-methyl-2-benzothiazylthio)-benzoic acid.

3. The rust-preventive compound of claim 1 wherein Y is selected from alkali metals and alkaline earth metals, and said alkali metals are selected from the group consisting of lithium, sodium and potassium; and said alkaline earth metals are selected from the group consisting of magnesium, calcium and strontium.

4. The rust-preventive compound of claim 3 wherein Y is an alkali metal, and said alkali metal is selected from the group consisting of sodium and potassium.

5. The rust preventive compound of claim 1 wherein Y is selected from ammonium and substituted ammonium groups.

6. The rust-preventive compound of claim 5 wherein Y is a quaternary ammonium group.

7. The rust-preventive compound of claim 6 wherein said quaternary ammonium group bears the general formula —H.Z, wherein Z is a substituent selected from the group consisting of ammonia, aliphatic amines, alicyclic amines, heterocyclic amines and polyethylene polyamines.

8. The rust-preventive compound of claim 7 wherein said aliphatic amines are selected monoethanolamine, diethanolamine and triethanolamine; said alicyclic amines are selected from cyclohexylamine and dicyclohexylamine; said heterocyclic amines are selected from morpholine and pyridine; and, said polyethylene polyamines are selected from diethylene triamine, triethylene tetramine and tetraethylene pentamine.

9. A rust-preventive composition comprising the compound of claim 1 in a suitable carrier.

10. A rust-preventive compound comprising benzothiazole-substituted carboxylic acids, and salts thereof, said compound possessing rust and corrosion inhibitive capability with respect to both iron and copper-based metals.

11. The compound of claim 10 wherein said benzothiazole-substituted carboxylic acids are selected from the group consisting of 2-benzothiazyl thioacetic acid, 6-amino-2-benzothiazyl thioacetic acid, 6-hydroxy-2- benzothiazyl thioacetic acid, 5-carboxy-2-benzothiazyl thioacetic acid, 2-benzothiazyl thioformic acid, 3-(4-methyl-2-benzothiazylthio)-propionic acid, 3-(6-hydroxy-2-benzothiazylthio)-propionic acid, 3-(4,6-dimethyl-2-benzothiazylthio)-propionic acid, 2-(2-benzothiazylthio)-propionic acid, 3-(5-chloro-2-benzothiazylthio)-propionic acid, 2-(4-methyl-2-benzothiazylthio)-propionic acid, 5-(2-benzothiazylthio)-valeric acid, 3-(2-benzothiazyl thio)-valeric acid, 5-(5,6-dihydroxy-2-benzothiazyl thio)-valeric acid, 5-(4-methyl-2-benzothiazylthio)-valeric acid, 3-(2-benzothiazylthio)-acrylic acid, 3-(4-methyl-2-benzothiazylthio)-acrylic acid, 4-(2-benzothiazylthio)-butyric acid, 4-(4-methyl-2-benzothiazylthio)-butyric acid, 4-(6-amino-2-benzothiazylthio)-butyric acid, 2-(2-benzothiazylthio)-benzoic acid, and 2-(4-methyl-2-benzothiazylthio)-benzoic acid 12. The compound of claim 10 wherein said salts are prepared with a substituent selected from a group of alkali metals, alkaline earth metals, ammonium and substituted ammonium compounds.

13. The compound of claim 12 wherein said alkali metals are selected from the group consisting of lithium, sodium and potassium; and said alkaline earth metals are selected from the group consisting of magnesium, calcium and strontium.

14. The compound of claim 13 wherein said substituent is an alkali metal and said alkali metal is selected from the group consisting of sodium and potassium.

15. The rust-preventive compound of claim 12 wherein said substituent is a quaternary ammonium group.

16. The rust-preventive compound of claim 15 wherein said quaternary ammonium group bears the general formula —H.Z, wherein Z is a substituent selected from the group consisting of ammonia, aliphatic amines, alicyclic amines, heterocyclic amines and polyethylene polyamines.

17. The rust-preventive compound of claim 16 wherein said aliphatic amines are selected monoethanolamine, diethanolamine and triethanolamine; said alicyclic amines are selected from cyclohexylamine and dicyclohexylamine; said heterocyclic amines are selected from morpholine and pyridine; and, said polyethylene polyamines are selected from diethylene triamine, triethylene tetramine and tetraethylene pentamine.

18. A rust-preventive composition comprising the compound of claim 10 in a suitable carrier.

* * * * *